United States Patent
Fujii et al.

(10) Patent No.: US 9,028,421 B2
(45) Date of Patent: May 12, 2015

(54) BLOOD FLOW IMAGE DIAGNOSING DEVICE

(75) Inventors: Hitoshi Fujii, Munakata (JP); Kenji Okamoto, Koga (JP); Noriyoshi Takahashi, Iizuka (JP); Hiroyuki Ishihara, Iizuka (JP)

(73) Assignee: Kyushu Institute of Technology, Fukuoka (JP)

( * ) Notice: Subject to any disclaimer, the term of this patent is extended or adjusted under 35 U.S.C. 154(b) by 430 days.

(21) Appl. No.: 13/254,754

(22) PCT Filed: Apr. 20, 2010

(86) PCT No.: PCT/JP2010/056980
§ 371 (c)(1),
(2), (4) Date: Sep. 2, 2011

(87) PCT Pub. No.: WO2010/131550
PCT Pub. Date: Nov. 18, 2010

(65) Prior Publication Data
US 2011/0319775 A1     Dec. 29, 2011

(30) Foreign Application Priority Data

May 13, 2009 (JP) .................................. 2009-116050
Oct. 27, 2009 (JP) .................................. 2009-246274

(51) Int. Cl.
*A61B 5/02* (2006.01)
*A61B 5/026* (2006.01)
(Continued)

(52) U.S. Cl.
CPC ............. *A61B 5/0261* (2013.01); *A61B 3/1233* (2013.01); *A61B 5/02007* (2013.01); *A61B 5/489* (2013.01)

(58) Field of Classification Search
None
See application file for complete search history.

(56) References Cited

U.S. PATENT DOCUMENTS 4,862,894 A * 9/1989 Fujii .............................. 600/479
5,074,307 A * 12/1991 Aizu et al. ..................... 600/479
(Continued)

FOREIGN PATENT DOCUMENTS

JP           02274221 A      11/1990
JP           04-242628 A      8/1992
(Continued)

OTHER PUBLICATIONS

H. Tagawa, et al., "Measurements of Blood Circulation in Retinal Vessels Using Laser Speckle Flowgraphy," Folia Ophthalmogica Japonica, 2000, pp. 121-125, vol. 51, No. 2.
(Continued)

*Primary Examiner* — Michael Kahelin
*Assistant Examiner* — Mitchell E Alter
(74) *Attorney, Agent, or Firm* — Sughrue Mion, PLLC

(57) ABSTRACT

A blood flow image diagnosis device which diagnoses a blood flow map by separating, on the basis of a plurality of blood flow maps covering a specified time including one or more cardiac beats, a blood flow of a surface layer blood vessel observed in a surface layer in an observation region of a body tissue from a background blood flow of a peripheral background region. The device distinguishably displays a first blood flow map of the surface layer blood vessel and a second blood flow map of the background blood flow. The device calculates and compares information on a blood flow including blood flow value, blood flow waveform, or blood vessel diameter in the first and second blood flow maps, and displays the calculated information.

18 Claims, 10 Drawing Sheets

(51) Int. Cl.
*A61B 3/12* (2006.01)
*A61B 5/00* (2006.01)

(56) References Cited

U.S. PATENT DOCUMENTS

| | | | | |
|---|---|---|---|---|
| 5,129,400 | A | * | 7/1992 | Makino et al. ............... 600/479 |
| 5,150,292 | A | * | 9/1992 | Hoffmann et al. ............ 600/431 |
| 5,163,437 | A | | 11/1992 | Fujii et al. |
| 5,240,006 | A | * | 8/1993 | Fujii et al. ................... 600/425 |
| 5,615,683 | A | * | 4/1997 | Toge et al. ................... 600/479 |
| 5,640,963 | A | * | 6/1997 | Tanaka ......................... 600/470 |
| 5,954,658 | A | * | 9/1999 | Gorti ............................ 600/504 |
| 8,277,384 | B2 | * | 10/2012 | Fine .............................. 600/485 |
| 2002/0058874 | A1 | | 5/2002 | Ono et al. |
| 2003/0097076 | A1 | * | 5/2003 | Nambu et al. ................ 600/504 |
| 2007/0263906 | A1 | * | 11/2007 | Fujii et al. ................... 382/115 |
| 2009/0005691 | A1 | * | 1/2009 | Huang et al. ................. 600/476 |
| 2009/0177098 | A1 | * | 7/2009 | Yakubo et al. ............... 600/504 |
| 2009/0202113 | A1 | | 8/2009 | Fujii et al. |
| 2010/0056936 | A1 | * | 3/2010 | Fujii et al. ................... 600/504 |
| 2010/0168585 | A1 | * | 7/2010 | Fujii et al. ................... 600/476 |
| 2012/0065525 | A1 | * | 3/2012 | Douniama et al. ........... 600/485 |

FOREIGN PATENT DOCUMENTS

| | | |
|---|---|---|
| JP | 5-28133 B | 4/1993 |
| JP | 5-28134 B2 | 4/1993 |
| JP | 08-112262 A | 5/1996 |
| JP | 2000-037351 A | 2/2000 |
| JP | 2002517269 A | 6/2002 |
| JP | 2003-164431 A | 6/2003 |
| JP | 2003-180641 A | 7/2003 |
| JP | 2006095350 A | 4/2006 |
| JP | 2008-237432 A | 10/2008 |
| JP | 2009-095350 A | 5/2009 |
| WO | 9963882 A1 | 12/1999 |
| WO | 2006/046627 A1 | 5/2006 |
| WO | WO 2007142055 A1 * | 12/2007 |
| WO | 2008/069062 A1 | 6/2008 |

OTHER PUBLICATIONS

Decision of Patent Grant issued Jun. 24, 2014 in Japanese Patent Application No. 2011-513293.

* cited by examiner

BLOOD FLOW IMAGE DIAGNOSING DEVICE

CROSS REFERENCE TO RELATED APPLICATIONS

This application is a National Stage of International Application No. PCT/JP2010/056980 filed Apr. 20, 2010 which claims priority to Japanese Patent Application No. 2009-116050 filed May 13, 2009 and Japanese Patent Application No. 2009-246274 filed Oct. 27, 2009, the contents of which are incorporated herein by reference in their entirety.

TECHNICAL FIELD

The present invention relates to a blood flow rate imaging device for measuring and imaging a blood flow rate on the basis of a speckle signal reflected from a body tissue obtained by irradiating the body tissue having blood cells with a laser beam wherein a new function for analyzing a blood flow imaging is added thereto.

BACKGROUND ART

Conventionally, the present inventors have developed a blood flow rate measuring device that irradiates with a laser beam a body tissue having blood cells such as an eye ground and a skin, leads random speckled patterns, i.e. speckle images, which are formed by interference of reflected light from the blood cells, onto an image sensor such as a solid-state image sensor (CCD or CMOS), sequentially captures and stores a large number of these speckle images at predetermined time intervals, selects a predetermined number of images from the large number of the stored images, calculates a value reflecting a time variation speed of output in each pixel of each image and then calculates the velocity of blood cells (blood flow rate) from the value.

In this kind of blood flow rate measuring device, the output variation speed of each pixel corresponds to a movement velocity of blood cells. Accordingly, a blood flow distribution in a body tissue can also be color-displayed on a monitor screen as a two-dimensional image (blood flow map) based on the value of the output variation calculated in each pixel. A blood flow map observed actually is composed of sequential blood flow maps calculated so as to become about 30 scenes per second. Hereinafter, the sequential blood flow maps are sometimes called as an original map. The blood flow map can be displayed as an animation. Therefore, this device has been put to practical use as a device for inspecting hemodynamics of an eye ground or skin (see Japanese Examined Patent Publication No. Hei 5-28133, Japanese Examined Patent Publication No. Hei 5-28134, Japanese Unexamined Patent Publication No. Hei 4-242628, Japanese Unexamined Patent Publication No. Hei 8-112262, Japanese Unexamined Patent Publication No. 2003-164431, and Japanese Unexamined Patent Publication No. 2003-180641).

In addition, the present inventors proposed a blood flow rate imaging device that analyzes a blood flow variation appearing at regular intervals synchronously with cardiac beats in each site within an observation field on the basis of sequential blood flow maps obtained between a few seconds in blood flow measurement, introduces a numerical value capable of distinguishing an arterial site with a steep rise waveform and a venous site with a waveform gradually going up and down, i.e., skewness, and displays an arterial pulse part and a venous pulse part on a blood flow map (see WO2008/69062 Pamphlet).

However, when the blood flow rate imaging device proposed by the present inventors is used to detect, for example, a blood flow of an eye ground, sequential original maps obtained by calculating a blood flow distribution actually are generally grainy as shown in FIG. 1 and outlines of blood vessels are composed of grains. These grains arise from facts that a speckle image for calculating a blood flow value intrinsically has much noise and a statistical error occurs since samples for measuring blood flow of each pixel are limited in number. There are essential differences on location and size of grains between a series of original maps. In other words, numerical values representing a blood flow rate in each pixel vary considerably in respective maps. It is known that a blood flow in an arterial blood vessel on a retina changes periodically by cardinal beats. A numerical value or a waveform thereof includes important information on a peripheral circulatory function. However, in order to detect the value or the waveform accurately, it is necessary to distinguish accurately whether each pixel of an original map obtained at a certain time is positioned in the retina vessel part in the surface layer or is positioned in the blood flow of the peripheral choroid and other tissues (background blood flow). Such distinction is difficult to perform on the basis of the original map with rough grains as shown in FIG. 1. Therefore, it has been a big problem to develop a method for distinguishing region of blood vessel running on a surface accurately, i.e., the retina vessel region, from a region of background blood flow.

Further, when distribution of skewness characterizing a blood flow waveform of an eye ground is required using the conventional blood flow rate imaging device as proposed in the WO2008/69062 Pamphlet, blood flow values in numerous pixels adjacent to a target pixel are taken into calculation so as to increase samples in number and reduce a statistical error. However, since the blood flow values are calculated based on pixels extracted from a region containing both a blood vessel part and a background tissue part that have a different waveform from each other, information on the blood flow waveforms are confused mutually. Consequently, when the distribution of skewness is displayed as an image, there is a problem that a waveform of a thin arterial blood vessel is difficult to distinguish, since it is buried in a waveform of tissue blood flow existing in the background. A waveform of a target blood vessel can be obtained by extracting a blood flow value along a course of a blood vessel and specifying skewness. As stated above, however, there has been a problem that it is difficult to find a method for extracting only blood vessels.

Further, using the conventional blood flow imaging device, a region called a rectangular rubber band such as a rectangular portion illustrated at the upper part of the center in FIG. 1 is set up manually along a course of a predetermined blood vessel in a blood flow map as shown in FIG. 1, and then, a blood flow waveform in the rubber band (refer to FIG. 2) or a distribution of blood flow rate in cross-section of blood vessel (refer to FIG. 3) is examined. The horizontal axis of FIG. 3 shows pixels. In such a method, it is necessary to select a straight blood vessel and, for examining a blood flow waveform, it is also necessary to set up the rubber band in an elongated form and exactly so as to match to the width of the blood vessel. For examining a cross-section of blood vessel, a straight blood vessel is also selected and a bit broader region in parallel to the blood vessel is set up, then, blood flow values are averaged in a direction of the blood vessel running to obtain a cross-sectional view of velocity distribution as shown in FIG. 3.

However, since most retina vessels are not straight as shown in FIG. 1, only limited blood vessels can be measured by the method setting up the rectangular region. In addition, very complicated work is required to set accurately a rectangular region on a blood vessel every time blood flow analysis is performed.

It has been considered that a relation between a diameter of arterial blood vessel and a blood flow waveform includes very important information for understanding not only an ocular disease but also systemic hemodynamics. Therefore, if a retina vessel can be selected freely to measure a blood flow waveform and an effective diameter thereof, it is of great significance. Accordingly, it has been a great problem to develop a method in which a meandering blood vessel can be analyzed as well as a straight blood vessel.

On the other hand, when a blood flow waveform in each site of an eye ground (observation region) is converted to a numerical value using skewness, the skewness is affected with a secondary peak and fluctuation of peak position in the waveform if they exist. Further, arterial blood flow waveforms upon rising and going down may relate to different factors regarding a peripheral circulatory function, respectively. Therefore, it is insufficient to characterize a blood flow waveform by only skewness, and thus it is also necessary to introduce other indices so as to judge holistically.

SUMMARY OF THE INVENTION

Problems to be Solved by the Invention

An object of the present invention is to provide a blood flow image diagnosis device which is obtained by applying and developing a conventional blood flow rate imaging device, comprising
a means that improves convergence of each value of blood flow in a surface layer of a body tissue (surface layer blood flow) and blood flow in a background (background blood flow) when a secondary peak of blood flow waveform appears or blood flow values vary a great deal and a means that distinguishes automatically a blood vessel region such as a meandering blood vessel for which it is difficult to measure a blood vessel diameter, and calculates and displays an average blood vessel diameter.

Means for Solving the Problems

The problems mentioned above can be solved by the present invention described in following embodiments 1 to 18.

The invention described in embodiment 1 is a blood flow image diagnosis device comprising:
a laser beam irradiation system that irradiates an observation region of a body tissue having a blood cell with a laser beam;
a light receiving system having a light receiver including a large number of pixels that detects reflected light from the observation region of the body tissue;
an image capture section that continuously captures a plurality of images for a specified time that is one or more cardiac beats on the basis of a signal from the light receiver;
an image storage section that stores the plurality of images;
an arithmetic section that calculates a blood flow rate within the body tissue from the time variation of the output signal of each pixel corresponding to the plurality of the stored images; and
a display section that displays the two-dimensional distribution of the calculation result as a blood flow map;

wherein
the blood flow image diagnosis device has a function for diagnosing the blood flow map,
the arithmetic section has a function that separates a blood flow of a blood vessel observed in a surface layer in the observation region of the body tissue (surface layer blood vessel) from a blood flow of a peripheral background region (background blood flow) on the basis of the plurality of blood flow map data covering the time that is one or more cardiac beats,
the display section has a function that distinguishably displays blood flow maps of respective portions,
the arithmetic section has a function that calculates and compares information on a blood flow including blood flow value, blood flow waveform or blood vessel diameter in said respective portions, and the display section has a function that displays the calculation result obtained in the arithmetic section.

In the present invention, taking characteristics of a blood flow map mentioned below into account, the passage "a blood flow of a blood vessel observed in a surface layer of a body tissue (surface layer blood vessel)" represents not only a blood flow but also a blood vessel itself located in a surface layer site such as a retina. But, the passage "a blood flow in a peripheral background region (background blood flow)" represents literally a blood flow of a choroid or other tissues surrounding the blood vessel in the surface layer site (background blood flow). That is, when the device of the present invention is used, blood vessels in the surface layer site of the body tissue such as a retina vessel can be clearly recognized. However, blood vessels in the background site such as a choroid vessel are difficult to recognize clearly and can be recognized only as a blood flow in the background site. Accordingly, in the present specification, the former is used as a term having the same meaning as "blood vessel" and the latter is used as a term meaning only "blood flow".

In the invention, needless to say, known features or means can be added to or incorporated into the blood flow image diagnosis device if necessary.

The invention described in embodiment 2 is a blood flow image diagnosis device according to embodiment 1, wherein the arithmetic section has a function that
calculates an amount of position-disparity between each map generated by movement of a measuring object regarding said plural blood flow map data,
obtains an average blood flow map by compensating the amount of position-disparity and superimposing,
distinguishes a range with higher blood flow from a range with lower blood flow than a predetermined threshold level,
excludes isolated points,
separates a series of high value points regarded as a blood flow of blood vessel in a surface layer from the others regarded as a background blood flow,
reflects thus-obtained information in each map,
extracts independently a blood flow of a surface layer blood vessel appeared on the surface layer site and a background blood flow of a background site in a predetermined region of a map, and
obtains information on the above blood flows in each site.

The invention described in embodiment 3 is a blood flow image diagnosis device according to embodiment 1, wherein the arithmetic section has a function that
obtains each waveform for a blood flow of a surface layer blood vessel and a background blood flow separated by the above function in one or more predetermined regions of a blood flow map, quantifies a feature of a blood flow waveform which appeared upon either an increase or decrease of blood flow variation by heart beat or features of both blood flow waveforms and displays and compares thus-obtained values with respect to each region.

The invention described in embodiment 4 is a blood flow image diagnosis device according to embodiment 1, wherein the arithmetic section has a function that obtains each skewness of blood flow waveform for a blood flow of a surface layer blood vessel and a background blood flow separated by the above function in one or more predetermined regions of a blood flow map, and displays and compares thus-obtained values with respect to each region.

The invention described in embodiment 5 is a blood flow image diagnosis device according to embodiment 1, wherein the arithmetic section has a function that obtains each blood flow waveform for a blood flow of a surface layer blood vessel and a background blood flow separated by the above function in one or more predetermined regions of a blood flow map, integrates a blood flow value in a time in which a waveform goes to a bottom from a peak, integrates a constant blood flow value indicated as (peak value−minimum value) in the same time, quantifies a feature of a blood flow waveform by obtaining a ratio of both integrated blood flow values, displays and compares values thus-obtained values with respect to each region.

The invention described in embodiment 6 is a blood flow image diagnosis device according to embodiment 1, wherein the arithmetic section has a function that obtains each blood flow waveform for a blood flow of a surface layer blood vessel and a background blood flow separated by the above function in one or more predetermined regions of a blood flow map, obtains an amplitude value of each blood flow waveform, quantifies a feature of a blood flow waveform by calculating a ratio of the amplitude value to the average blood flow value, and displays and compares thus-obtained values with respect to each region.

The invention described in embodiment 7 is a blood flow image diagnosis device according to embodiment 1, wherein the arithmetic section has a function that specifies one or more regions containing a surface layer blood vessel in a blood flow map, separates a blood flow of the surface layer blood vessel from the background blood flow by the above function, extracts a blood flow value in each region, and calculates independently each average value on the surface layer blood vessel and the background blood flow, and a function that displays and compares thus-obtained values with respect to each region.

For example, a rectangular region may be set as a region containing a surface layer blood vessel in a blood flow map.

The invention described in embodiment 8 is a blood flow image diagnosis device according to embodiment 1, wherein the arithmetic section has a function that separates the surface layer blood vessel from the background blood flow according to the method described in the embodiment 7, Calculates the total number of pixels in a region corresponding to the surface layer blood vessel, thereby calculates a numerical value proportional to a diameter of the surface layer blood vessel, and displays and compares the numerical value.

The invention described in embodiment 9 is a blood flow image diagnosis device according to embodiment 1, wherein the arithmetic section has a function that separates the surface layer blood vessel from the background blood flow according to the method described in the embodiment 7, specifies borderlines between the surface layer blood vessel and the background blood flow existing in both sides thereof, calculates a diameter of the surface layer blood vessel on the basis of the interval of the borderlines, and displays and compares the thus-obtained value.

The invention described in embodiment 10 is a blood flow image diagnosis device according to any one of embodiments 3-9, wherein the blood flow image diagnosis device has a function that compares results calculated according to any one of embodiments 1-9 with results calculated in the same manner based on other blood flow image data with a different measurement date or time, calculates an increase-decrease rate of the former based on the latter, and displays and compares the thus-obtained value.

The invention described in embodiment 11 is a blood flow image diagnosis device according to any one of embodiments 1-10, wherein the device has a function that, when a mask is made to separate a surface layer blood vessel from a background blood flow, makes the mask by utilizing light and dark parts of a retina image which is obtained by irradiating an eye ground with an incoherent light, applies the mask to each blood flow map, and obtains information on said blood flow in each site.

The invention described in embodiment 12 is a blood flow image diagnosis device according to embodiment 1, wherein the arithmetic section has a function that specifies one or more rectangular regions containing a surface layer blood vessel in a blood flow map so as to have a longer direction along a course of the blood vessel, separates a blood flow of a surface layer blood vessel from a background blood flow by the function set forth above, totals a value that is obtained by subtracting a background blood flow value from a blood flow value in each pixel in a region corresponding to the surface layer blood vessel, calculates a value proportional to a blood flow volume of the surface layer blood vessel by dividing the sum by a longitudinal pixel count of the rectangular region, displays the thus-obtained value, and compares the value in each region mutually or with a value measured at a different time.

The invention described in embodiment 13 is a blood flow image diagnosis device according to embodiment 12, Wherein the device has a function that analyzes an appearance that the value proportional to a blood flow volume obtained by the arithmetic section changes during the measurement, displays analysis results as a waveform of blood flow volume, and analyzes and quantifies a feature of the waveform.

The invention described in embodiment 14 is a blood flow image diagnosis device according to embodiment 1, wherein the arithmetic section has a function that, in a region containing a number of retina vessels extending from an optic nerve head to all sides, distinguishes an artery and a vein by analyzing a blood flow waveform in a blood vessel crossing a borderline of the region, analyzes a blood flow volume and/or a blood flow waveform, respectively, and displays analysis results near each blood vessel, saves them as data files or compares them with those measured on a different date.

The present invention described in embodiment 15 is a blood flow image diagnosis device according to embodiment 1, wherein the arithmetic section has a function that, in a region containing a number of retina vessels extending from an optic nerve head to all sides, calculates each total blood flow volume of an artery and a vein going in and out through a boundary of the region, and compares a value of a ratio of both total blood flow volumes or compares the total blood flow volume with one measured on a different date.

The invention described in embodiment 16 is a blood flow image diagnosis device according to embodiment 1, wherein the arithmetic section has a function that, in a region containing a number of retina vessels extending from an optic nerve head to all sides, calculates a ratio of a blood flow volume to a blood vessel diameter regarding a blood vessel passing through the region, and displays results thus calculated using a figure or color.

The invention described in embodiment 17 is a blood flow image diagnosis device according to embodiment 1, wherein the arithmetic section has a function that, in surface layer blood vessels crossing mutually or a piece of a surface layer blood vessel with branched vessels in a blood flow map, analyzes a blood flow volume or a blood flow waveform of each blood vessel, and displays analysis results near or in each blood vessel, saves them as data files or compares them with those measured on a different date.

The invention described in embodiment 18 is a blood flow image diagnosis device according to embodiment 1, wherein the arithmetic section has a function that, in a surface layer blood vessel in a blood flow map, analyzes each time-dependent waveform regarding a blood flow volume and a blood flow value of the surface layer blood vessel, calculates a difference of a peak position between these waveforms, and displays results thus calculated using a figure or color.

The invention described in the above embodiment 1 relates to a device with an additional function that separates a surface layer blood vessel from a background blood flow, displays respective blood flow maps distinctively, calculates and compares information on a blood flow such as a blood flow value, blood flow waveform and blood vessel diameter in the surface layer site and the background site and displays calculation results thus obtained.

The invention described in the embodiment 2 relates to a technique that separates a surface layer blood vessel from a background blood flow using specifically an average blood flow map.

The invention described in the embodiment 3 relates to quantifying a wavy feature of each blood flow map separated according to the embodiment 1.

The inventions described in the embodiments 4, 5 and 6 relate to displaying a wavy feature as a ratio to an average value with respect to skewness, an area ratio or an amplitude value, respectively.

The invention described in the embodiment 7 relates to displaying an average blood flow of a surface layer blood vessel separated according to the embodiment 1.

The invention described in the embodiment 8 relates to evaluating and displaying an increase-decrease of blood vessel diameter based on total pixels corresponding to the surface layer blood vessel.

The invention described in the embodiment 9 is characterized in specifying borderlines on both sides of a surface layer blood vessel and reading a diameter of the surface layer blood vessel on the basis of the interval of the borderlines.

Further, the invention described in the embodiment 10 is characterized in calculating a ratio of increase-decrease upon comparing calculation results obtained according to any one of the embodiments 1-9 with those on other blood flow image data measured on a different date and displaying it.

The invention described in the embodiment 11 relates to a technique for making a mask by using something other than an average blood flow map.

The inventions described in the embodiments 12, 13, 17 and 18 are characterized in calculating a value proportional to a blood flow volume of a surface layer blood vessel (RFV) to display, compare or analyze.

The inventions described in the embodiments 14, 15 and 16 are characterized in applying the invention described in the embodiment 1 to a region containing a number of retina vessels extending from an optic nerve head to all sides.

Effects of the Invention

Using the device of the present invention, it becomes possible to separate a blood flow waveform of a retina vessel from one of a background tissue so as to analyze them, though it has not been possible to separate them clearly until now. Further, it is possible to distinguish an artery from a vein more accurately by grouping data along a course of each blood vessel extending circumferentially from an artery and a vein in the center. Also, in the case that a blood flow waveform has a secondary peak or in the case of a region having a highly-dispersive and complicated blood flow waveform which generally contains many points deviated greatly therefrom, it is possible to obtain a map wherein a surface layer blood flow or a retina vessel is distinguished from a background blood flow or a blood vessel of background tissue.

Conventionally, it has not been possible to measure a diameter of meandering retina vessels by setting a rubber band thereto. However, by determining a center line of blood vessel cut out using a specified mask and, subsequently, measuring a distance to an edge of the mask therefrom, it is possible to presume an inside diameter of meandering blood vessels and thereby it is also possible to evaluate a blood circulation effect. Further, since it is possible to separate an intravascular portion from a background tissue so as to evaluate each blood flow waveform and blood flow volume, there can be provided new information for evaluating functions of the circulatory system. In particular, an accurate observation of a blood flow waveform of an artery is considered extremely effective for diagnosing arteriosclerosis.

EMBODIMENT TO CARRY OUT OF THE INVENTION

Figure 17:
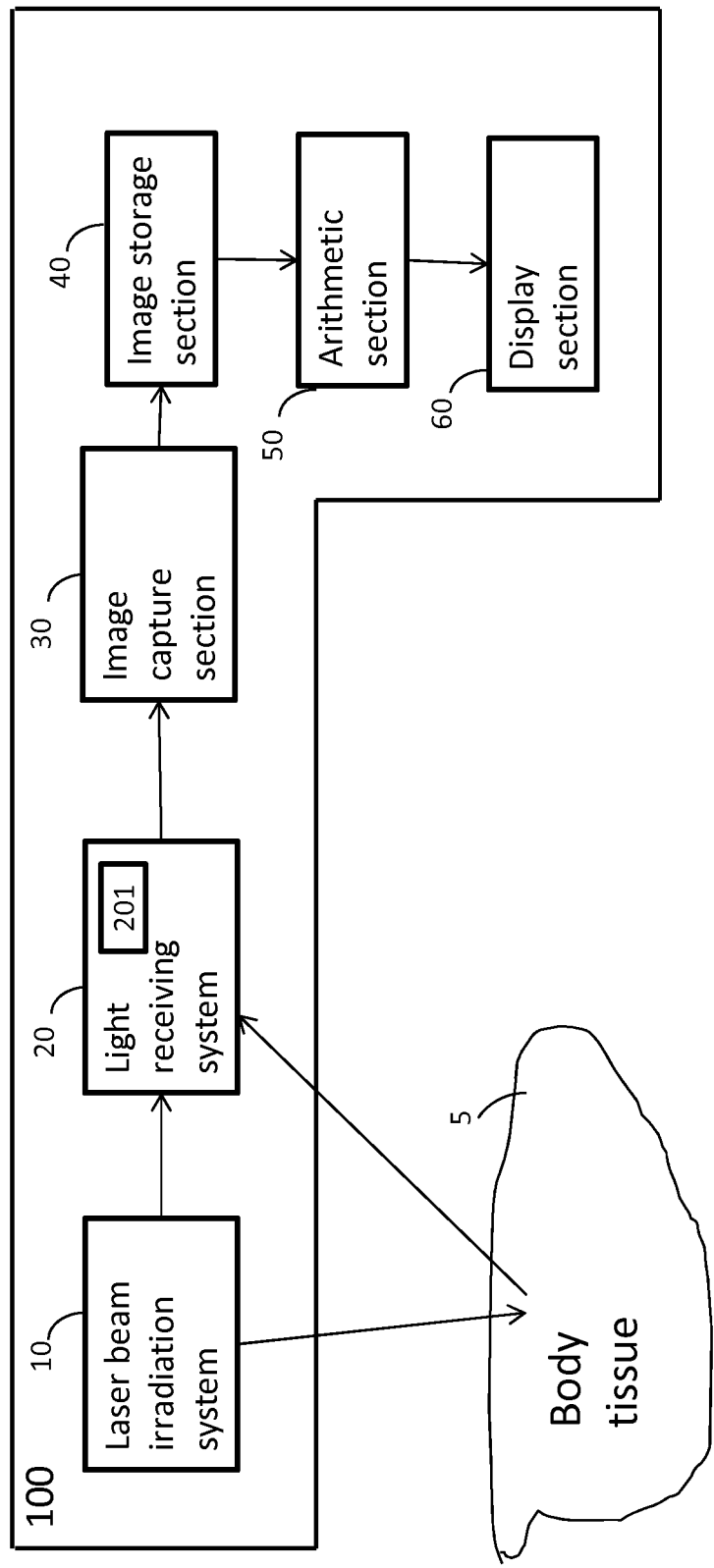
FIG. 17 illustrates a configuration of a blood flow image diagnosis device according to an exemplary embodiment.

As shown in FIG. 17, a blood flow image diagnosis device 100 of the present invention comprises a laser beam irradiation system 10 that irradiates a body tissue 5 having a blood cell with a laser beam;

a light receiving system 20 having a light receiver 201 including a large number of pixels that detects reflected light from the body tissue 5;

an image capture section 30 that continuously captures a plurality of images for a specified time that is one or more cardiac beats on the basis of a signal from the light receiver 201;

an image storage section 40 that stores the plurality of images;

an arithmetic section 50 that calculates a blood flow rate within the body tissue from the time variation of the output signal of each pixel corresponding to the plurality of the stored images; and a display section 60 that displays the two-dimensional distribution of the calculation result as a blood flow map.

Further, the arithmetic section 50 of the blood flow image diagnosis device 100 contains an additional function that separates a blood flow of a blood vessel observed in a surface layer of the body tissue (surface layer blood vessel) from a blood flow of a background region surrounding the surface layer blood vessel (background blood flow) and displays distinctly each blood flow on a blood flow map in the display section 60. For example, each blood flow map can be displayed side-by-side or sterically in the direction of depth as a separate image in the display section 60. When such a function that displays each map separately is provided to a display section 60, it makes possible to overview at a glance a difference between an average blood flow value in each site and one of a previous measurement, thereby to utilize the difference for diagnosis.

As a method for separating a blood flow in a surface layer of body tissue, e.g., a blood flow of a retina vessel obtained therefrom, from a blood flow existing in a background, i.e., background blood flow on the basis of a plurality of images for a specified time that is one or more cardiac beats, the following methods are specifically exemplified.

Figure 1:
FIG. 1 is a diagram indicating one example of a series of original maps obtained by observing a blood flow of an eye ground and calculating a blood flow distribution.
Figure 2:
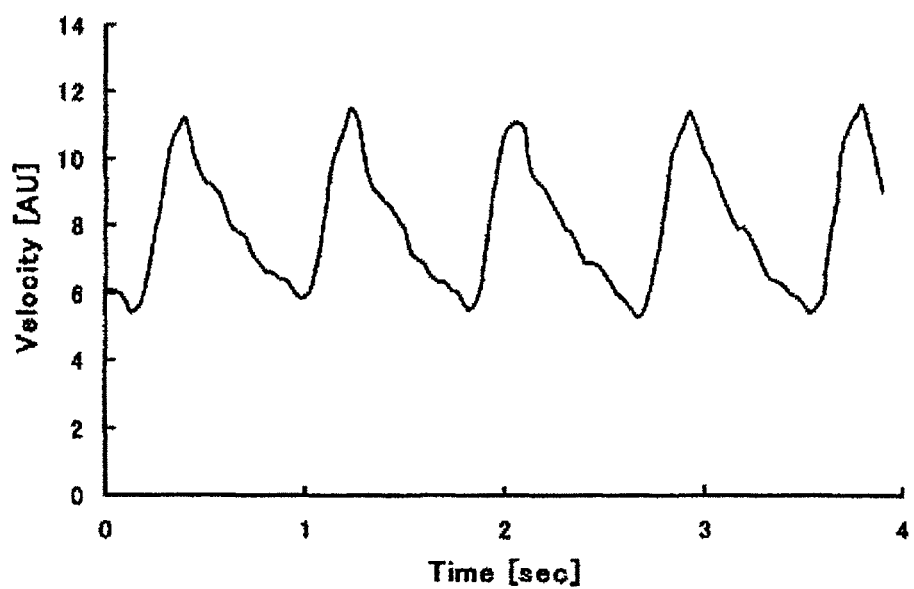
FIG. 2 is a diagram indicating a blood flow waveform in the rectangular rubber band set up along a course of a predetermined blood vessel in a blood flow map shown in FIG. 1.
Figure 3:
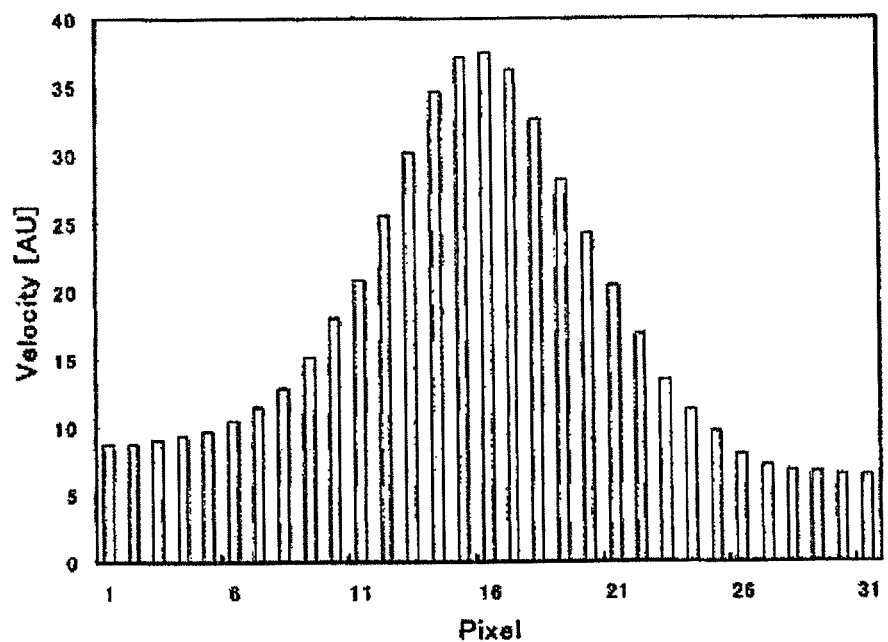
FIG. 3 is a diagram indicating a blood flow rate distribution in a cross-section of the blood vessel in the rectangular rubber band shown in FIG. 1.
Figure 4:
FIG. 4 is a diagram indicating one example of average blood flow maps obtained by calculating an amount of disparity between each original map, compensating an amount of movement and superimposing.

An amount of disparity between each original map containing visual fixation disparity or fixation movement is calculated, and subsequently the original maps are compensated by the amount of disparity, and then superimposed. This operation is called as tracking. A superimposed result is an average blood flow map as shown in FIG. 4. The map contains extremely limited rough grains compared with FIG. 1 since it is made by superimposing a number of original maps to average. Therefore, borderlines of the blood vessel can be distinguished clearly in the map.

Figure 5:
FIG. 5 is a diagram indicating one example of mask images.

For example, a binary image is made by specifying a pixel with a blood flow value more than a certain threshold level as 1 and a pixel with a blood flow value less than the threshold level as 0. Then, by excluding isolated points as noise, a mask image as shown in FIG. 5 is obtained for cutting out a blood vessel part. In the above tracking treatment, there are calculated and saved data on an amount of disparity and a relative position of an average blood flow map with respect to all original maps from the first to the last. Therefore, a mask pattern displayed on the average blood flow map enables one to extract accurately a blood vessel part by superimposing it upon any original map with a known relative position correlation.

When a blood flow waveform is measured regarding a specified blood vessel in a blood flow map, a region containing an objective blood vessel for analysis is set roughly. Thereby, according to the method set forth above for extracting a blood vessel, it is possible to extract only a value in a blood vessel or only a waveform of a background blood vessel layer. Further, both blood flow distributions can be displayed sterically back and forth. Accordingly, unlike the conventional method, the present invention needs neither choosing a linear blood vessel nor paying attention for fitting a position. Consequently, objects for analysis can be enlarged and an efficiency of analysis operation can be improved.

Since the invention of the device proposed previously by the present inventors discloses only a rubber band with a simple form such as a rectangular form, it is difficult to draw a curve rubber band along a curve of a blood vessel for measuring a blood flow of retina vessels. Therefore, it is necessary to find out a linear blood vessel as much as possible so that a rectangular rubber band can be set thereon so as to measure the blood flow value. However, those problems can be solved by the method or means set forth above of the present invention.

For example, when a map of skewness which is one of indices characterizing a waveform is required for a blood flow of an eye ground, statistical errors raise a variation in value and an image quality of the map deteriorates unless, in calculating the skewness on a certain pixel, the calculation includes data on a number of peripheral pixels as mentioned above. However, the incorporation of the data causes a decrease of spatial resolution, and thereby information on a thin blood vessel disappears. By contrast, use of the mask set forth above enables a waveform of each site to be taken separately by extracting only a value on a blood vessel within a specified range regarding every site from the upstream to the downstream of a blood vessel extending gradually from the center of a papillary edge to the periphery as shown in FIG. 5. For example, regions are set at some points around a blood vessel stricture part toward the downstream from the upstream and blood flow waveforms obtained from respective regions are compared. The comparison can be utilized in various diagnoses such as understanding of disease condition and confirmation of therapeutic gain.

An eye ground blood vessel flow imaging device in practical use at present has a display function called "cardinal beat map" that, taking visual fixation disparity into account, superimposes original maps over a number of cardinal beats so as to average them. By superimposing the mask set forth above upon the cardinal beat map, it becomes possible to take accurately and directly a waveform at one cardinal beat.

Figure 6:
FIG. 6 is a diagram indicating a rectangular region set up a bit broadly in a curve part of a blood vessel.

Even though a blood vessel on a retina is meandering, it is possible to read a blood flow rate or to specify a cross section of the blood vessel by using the mask set forth above. For example, a rectangular region is set a bit largely at a curve portion of a blood vessel as shown in FIG. 6, and subsequently, a mask is made to average a blood flow value in each pixel in the portion corresponding to the blood vessel. Thereby, an average blood flow rate in the blood vessel is determined. Since a total of pixels in the portion corresponding to the blood vessel is a value proportional to a diameter of the blood vessel, an increase of the value compared with a previous value can be diagnosed as a vascular dilation.

Figure 7:
FIG. 7 is a diagram explaining a method wherein a blood vessel is converted to a straight line with regard to the rectangular region shown in FIG. 6.
Figure 8:
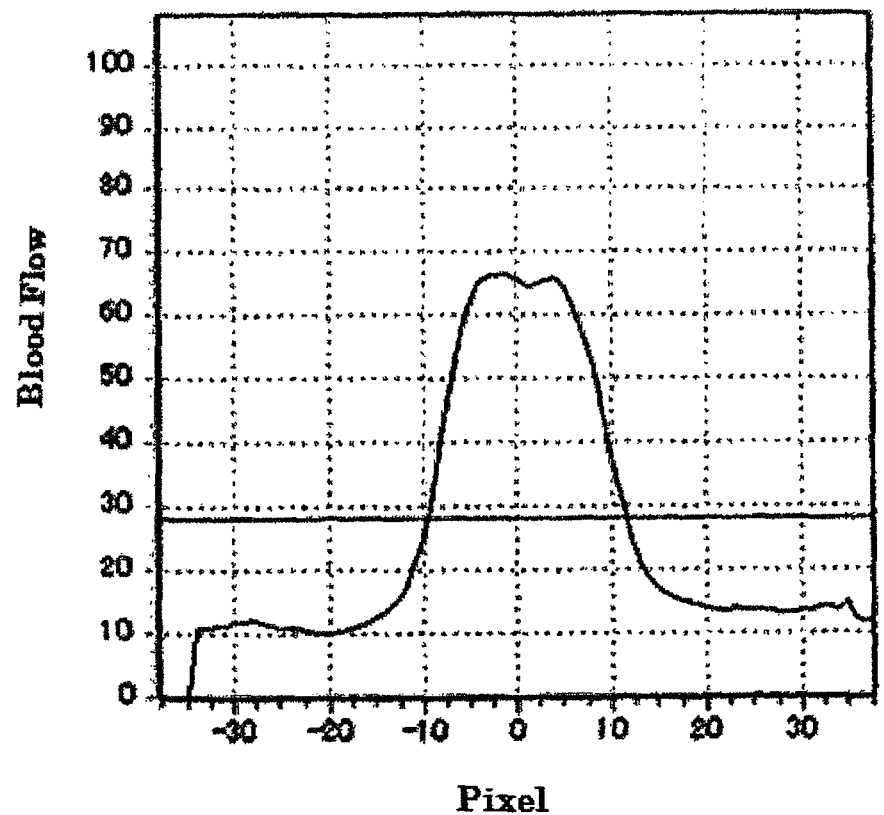
FIG. 8 is a diagram explaining a method for obtaining a blood flow rate distribution in a cross-section of a blood vessel and an average blood vessel diameter by averaging a blood flow distribution converted to a straight line as shown in FIG. 7.

In order to obtain a blood flow rate distribution in a cross section of a meandering blood vessel, the blood vessel may be converted to a straight line as follows. FIG. 7 illustrates a blood vessel converted to a straight line, taking out the rectangular portion shown in FIG. 6. First, all data in the rectangular region shown in FIG. 6 are extracted and rearranged so that a long axis direction and a short axis direction constitute a column and a row, respectively. Considering a position with the highest value as a center of a blood vessel, the rows are moved from side to side so that the highest values align straight up and down. Consequently, the blood vessel can be converted to a straight image as shown in FIG. 7. It is understood that, in FIG. 7, the peripheral portion of the blood vessel in FIG. 6 is undulated in the reverse direction due to linearizing the blood vessel. Two vertical lines drawn along the blood vessel indicate edges of the blood vessel read from FIG. 7 which correspond to borderlines of the blood vessel and the background blood flow on both sides of the blood vessel. These borderlines enable a diameter of the blood vessel to be presumed. Further, FIG. 8 is a diagram showing a mean value obtained by averaging a value of each row in the direction of the column regarding the matrix of data constituting the image shown in FIG. 7. It is possible to measure and compare an effective diameter of a blood vessel on the basis of this cross sectional diagram.

As set forth above, an average blood flow map is improved in the decrease of rough grains or granular structure compared with an original map. However, even with the average blood flow map, a centerline of a blood vessel does not correspond to the highest value of blood flow in many cases. In such a case, a diameter of a blood vessel can be determined by specifying borderlines on both sides of a blood vessel represented in a mask so as to measure an interval of both borderlines. Further, in the case of equipping a function that calculates a diameter of blood vessel along a course of a blood vessel shown in FIG. 7 and evaluates uniformity thereof, it also becomes possible to detect a vascular narrowing part due to cholesterol or the like. Thus, the function that measures a diameter of a blood vessel in the present invention can be utilized not only for diagnosis in ophthalmology but also for diagnosis in internal therapy such as hematogenous disorder caused by adult disease. In the present invention, the simplest way is setting a rectangular region along a course of a blood vessel. However, even when the region is set in other forms such as oval, it is possible to analyze a blood vessel diameter by specifying in advance a direction where the blood vessel runs or equipping software for recognizing the direction.

As described above, it is understood that the present invention enables information such as an average blood flow rate and a diameter of a retina vessel and a waveform representing a time variation of a blood flow rate to be taken out. However, in a clinical setting, it is often desired to understand an increase-decrease of blood flow volume of a blood vessel. In order to take out information on a blood flow volume, focusing on a branched portion of a blood vessel as shown in FIG. 9, a condition that blood flow volume is preserved before and after the branching of the blood vessel was examined in detail based on actual blood flow map data.

Since a retina vessel can be separated from a region of background blood vessels, taking into account that a numeral value obtained in the retina vessel part is raised by the effect of background blood flow, a blood flow volume of the retina vessel can be estimated by deducting the value of the background blood flow.

Figure 9:
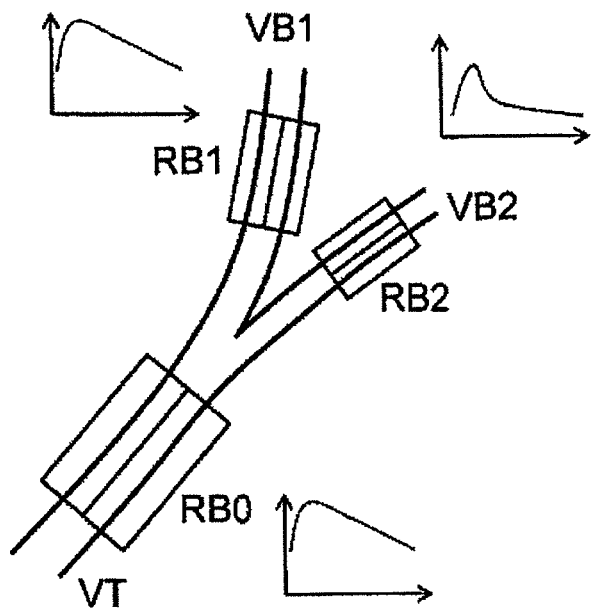
FIG. 9 is a diagram indicating a state that rubber bands RB0, RB1 and RB2 are set to a parent blood vessel VT, branched vessels VB1 and VB2, respectively, in a branched part of a blood vessel and blood flow waveforms in the respective parts.
Figure 10:
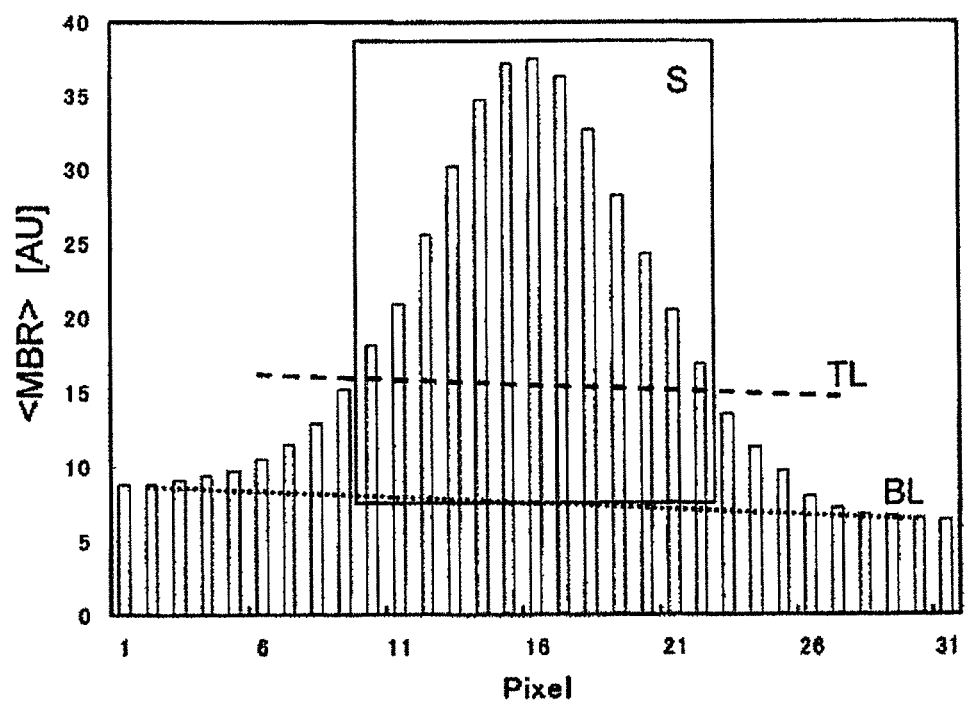
FIG. 10 is a diagram indicating a blood flow distribution in a cross-section of a blood vessel and explaining how to convert to a blood flow volume.

In a branched part of a blood vessel as shown in FIG. 9, rubber bands RB0, RB1 and RB2 are set along each course of a parent blood vessel VT and branched vessels VB1, VB2, respectively. According to the method set forth above, each blood vessel is converted to a straight line, mean blur rate (MBR), i.e., a mean value in the direction of the blood flow is plotted to obtain a blood flow rate distribution in the direction of the cross section of the blood vessel as shown in FIG. 10. Further, as shown in FIG. 10, a threshold level TL drawn in the dashed line which separates a blood vessel site or region from a background site or region is set properly, and the total of bar charts in the square frame S is considered as a value of the retina vessel. Since the value is considered to be raised by a value of background blood flow, a value of the baseline BL, drawn in the short dashed line, indicating the level thereof is deducted. Finally, a total of bar charts over the baseline in the square frame S, that is, only the value in the square frame S is considered as a blood flow component of a retina vessel. The total of these values is called Relative Flow Volume (RFV) in the present invention.

Figure 11:
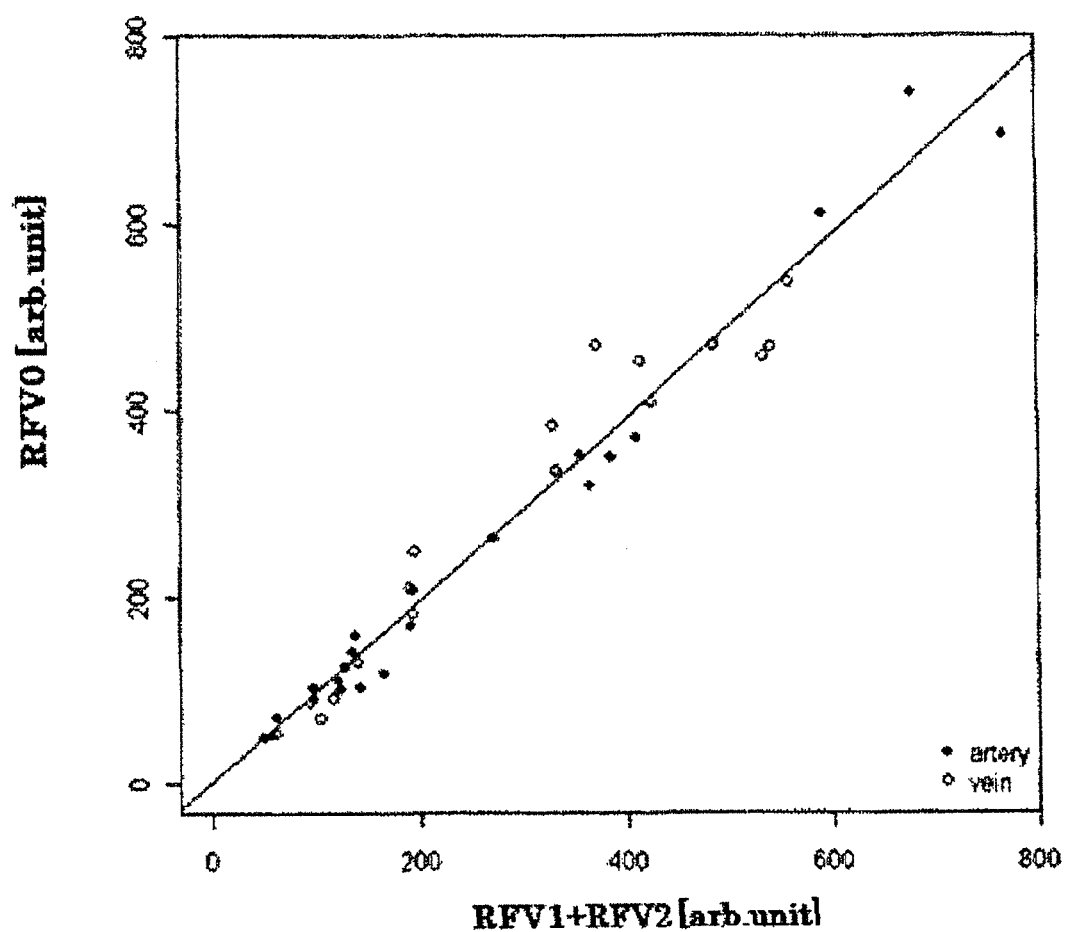
FIG. 11 is a diagram plotting results of correlation between RFV0 and RFV1+RFV2 examined about eye ground blood flow maps of five healthy adults.

In each region of RB0 to RB2, respective RFV values, i.e. RFV0, RFV1 and RFV2, were calculated, and then a correlation between RFV0 and RFV1+RFV2 was examined for eye ground blood flow maps of five healthy adults. Results are shown in FIG. 11. The results indicate a high enough correlation even when taking individual specificity into account. FIG. 9 shows a branching portion of an artery. But, taking into account a high correlation in a vein as well as in the artery as shown in FIG. 11, it is understood that the blood flow volume represented by RFV value is also preserved at the confluence part of the vein. Accordingly, there exists the law of conservation that the RFV value obtained by the above calculation is preserved before and after the branching of blood vessel in both the artery and the vein, and therefore it is understood that the value can be utilized as an index of blood flow volume.

In the above calculation of RFV value, first a blood flow rate distribution in a cross-section is calculated by averaging values in the direction of the course of a blood vessel, then, a baseline is specified on the basis of the values in the surroundings of the blood vessel, the value of the baseline is deducted and a sum total is calculated in the direction of the cross-section. In place of the calculation, values over a certain threshold level are sampled, then, a background blood flow component is deducted from each value, and subsequently, a sum total is calculated to be divided by a pixel count corresponding to the length of the centerline of the rubber band along the course of the blood vessel. By using the value thus obtained in this way, it is also possible to obtain similar results.

RFV value, i.e. blood flow volume can be also calculated for the original maps and the cardinal beat maps set forth above besides the average blood flow maps. In such a case, it is possible to observe a time variation of RFV value. Needless to say, a wavy feature of the time variation of RFV value can be quantified and compared according to the methods disclosed in any one of embodiments 4 to 6. In the case that blood flow volume is not conserved at a branching portion of blood vessel or respective vessels have different blood flow waveforms or different numerical values characterizing the blood flow waveforms, there is a high possibility that blood circulation is being impaired by some sort of cause.

For example, as shown in FIG. 9, when one of the branched blood vessels is greatly different in blood flow waveform or RFV waveform compared with those of the parent blood vessel, there is a high possibility that the branched blood vessel has an increased vascular resistance in an anterior position compared with the other. Also, in a place where an artery intersects with a vein, it is possible to diagnose whether or not blood circulation is being impaired at the intersection part by comparing blood flow waveforms of four sites in total located in anterior and posterior positions of the intersection. A function that compares an index representing a feature of blood flow waveforms obtained in plural regions of a retina vessel, e.g., skewness value, can be effectively utilized for diagnosing hemodynamics.

Figure 12:
FIG. 12 is a diagram indicating a rubber band having concentric circles drawn in a region containing an entire papillary edge.

As shown in FIG. 12, a rubber band having concentric circles containing an entire papilla is drawn and all blood vessels in the region with a doughnut shape between both circles are extracted. Then, a peripheral background blood flow component is deducted from a value of each blood vessel region and a sum total is calculated. Finally, the sum total is divided by L, i.e., a length of blood vessel along a course thereof. The thus-obtained value is the RFV value of each blood vessel. Since an artery can be distinguished from a vein on the basis of a blood flow waveform, it is possible to obtain distinctly each blood flow volume of the artery extending from a center of a papillary edge to an area surrounding a retina and the vein returning from the surrounding area toward the center of the papillary edge. Since a ratio of both volumes has an individual specificity, the ratio can be utilized as an index that represents circulatory dynamics of a retina blood flow. However, the RFV value is absolutely a relative value proportional to the blood flow volume. Therefore, it is affected by peripheral scattering tissues such as thickness of arterial wall or the like. In other words, it is understood that, by examining a difference between respective RFV values in an artery and a vein that have basically equal total blood flow volumes, the difference can be utilized as an index representing circulatory dynamics of a retina blood flow.

According to the methods set forth above, it becomes possible to take information such as a diameter, an average blood flow rate (relative value) and a blood flow volume (relative value) of a blood vessel like a retina vessel. However, these values are slightly affected by the thickness of the blood vessel wall. For example, although a blood flow volume of a piece of a blood vessel is basically conserved unless the vessel branches, the blood flow volume taken according to the above method varies by location in some cases. The cause is considered to relate to non-uniformity of the thickness of a blood vessel wall. On the contrary, the variation of the blood flow volume can be utilized to find a vascular narrowing part.

By drawing a rectangular and long rubber band along a piece of a blood vessel, dividing it into some segments, obtaining information in each segment such as a blood vessel diameter, an average blood flow rate, a blood flow waveform, an index representing a feature thereof and a blood flow volume, and displaying them along the course of the blood vessel, the above non-uniformity can be evaluated easily so that abnormal sites become easily specified.

Thus, by separating a surface layer blood vessel such as a retina vessel in a body surface layer from a background blood flow in background portions, measuring a blood vessel diameter, an average blood flow rate, a blood flow volume and a time variation thereof, and comparing respective values in each site or calculating a ratio on the basis of each measured result such as a ratio of blood vessel diameter to blood flow volume, it becomes possible to analyze in detail the dynamic state of a blood flow which has not yet been detected.

Recently, it has been found that a blood flow waveform changes with aging and the cause has been considered to be the influence of peripheral vascular resistance. The present inventors achieved some results by trying to quantify a blood flow waveform using skewness as disclosed in the WO2008/69062 Pamphlet. However, as set forth below, it has been found that actual waveforms have a secondary peak upon going down or a slight difference in the inclination upon rising. Skewness enables a difference of blood flow rate variation to be grasped roughly, but it is not necessarily sufficient to quantify a detailed variation of waveform. According to the present invention, some indices explained below are newly designed to make up for the insufficiency.

Figure 13:
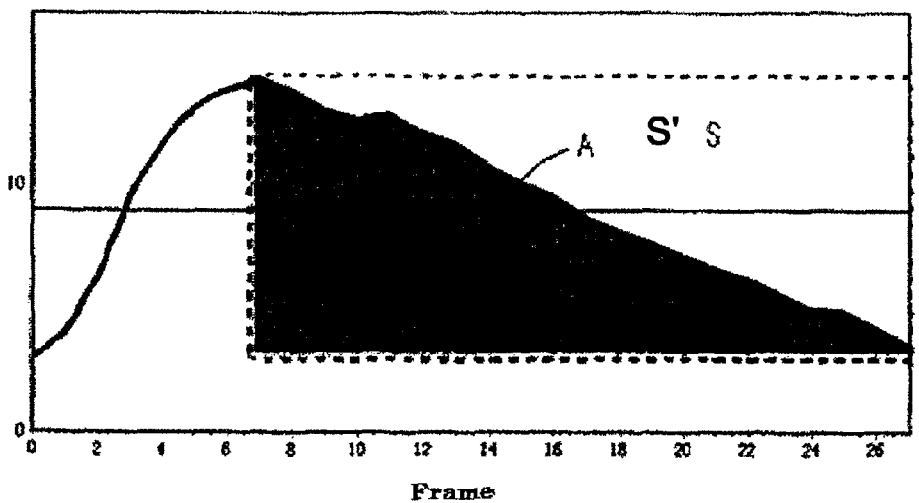
FIG. 13 is a diagram explaining a feature of a blood flow waveform when a blood flow descends.

It has been recently found that the blood flow waveform upon going down tends to be convex upward in youth and tends to become convex downward with aging. In order to quantify this feature, a numerical value is introduced wherein the value is obtained by integrating a blood flow value from a peak to a bottom as shown in FIG. 13, indicating the integrated value as A and dividing A by area S' of the part enclosed in the dashed line, that is, (peak value−minimum value)×number of frames. If the waveform is convex upward, this area ratio becomes greater than ½, while if it is convex downward, this area ratio becomes smaller than ½. In the same manner, using the formula A/(S'−A), if the waveform is convex upward, the numerical value becomes greater than 1, while if it is convex downward, it becomes smaller than 1. Regarding the blood flow waveform upon rising, it is also possible to specify whether the waveform is convex upward or downward using either of these area ratios in a similar way.

Figure 14:
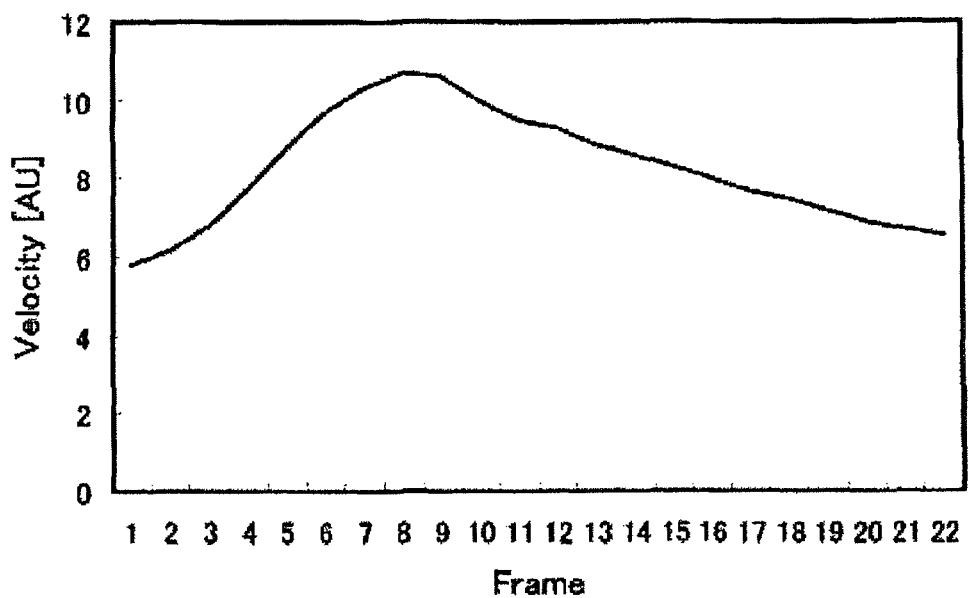
FIG. 14 is a diagram indicating a feature of a blood flow waveform in subjects in their sixties.
Figure 15:
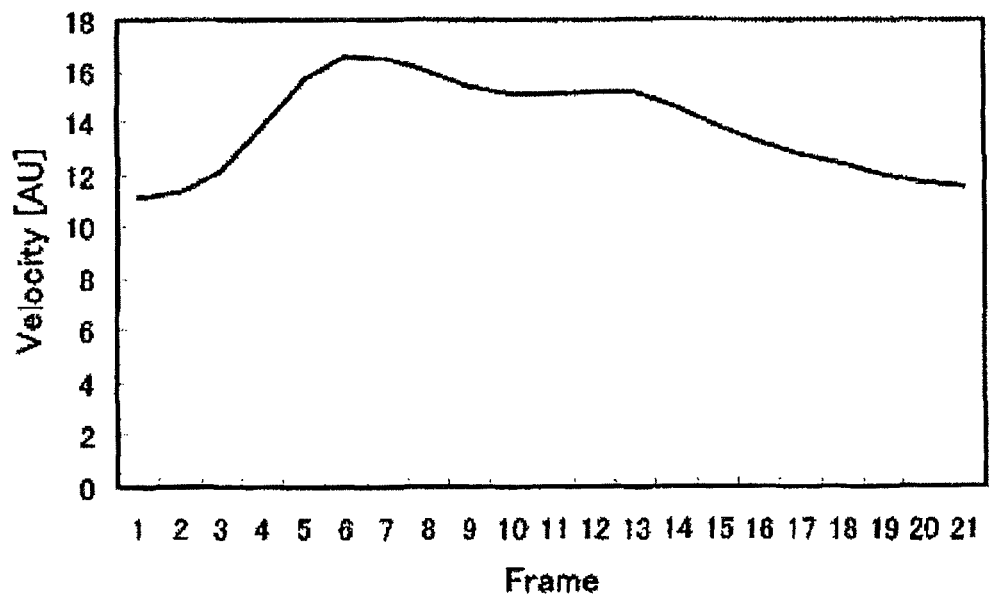
FIG. 15 is a diagram indicating a feature of a blood flow waveform in subjects in their twenties.

As an example that blood flow waveform of eye ground changes with aging, blood flow waveforms of sixty-something and twenty-something subjects are indicated in FIG. 14 and FIG. 15, respectively. These waveforms are based on the above "cardinal beat maps" of an optic nerve head tissue representing a waveform at one cardinal beat. There can be recognized at a glance the following differences between them.

(1) A time reaching a peak point becomes longer at aging. That is, a mean gradient decreases.

(2) A waveform upon rising shows a shape like an S character in the case of youth, while it goes up straight in the case of elderly people.

(3) A secondary peak often appears upon going down in the case of youth.

(4) Amplitude of variation is smaller in youth than in elderly people. That is, the youth has a greater amount of constant flow component that does not vary with a heartbeat.

The above feature described in (1) can be quantified by measuring a time reaching the highest point. The features described in (2) and (3) can be quantified by examining a shape of a secondary differentiation curve of a waveform. The feature described in (4) can be quantified by dividing an amplitude of variation by a mean value. These numerical values can be utilized to quantify peripheral vascular resistance and elasticity of a blood vessel, that is, degree of progress of arterioscleroses. Therefore, they can be utilized for diagnosis.

Figure 16:
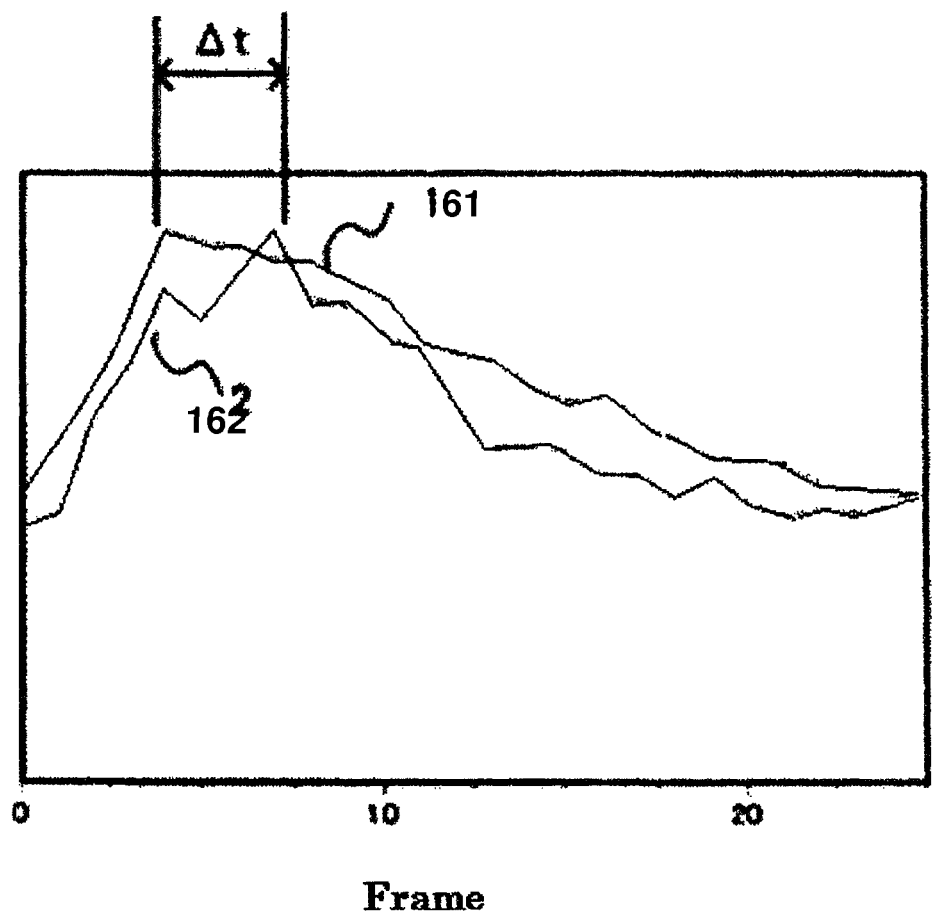
FIG. 16 is a diagram indicating a difference between a blood flow waveform and a RFV waveform.

The degree of progress of arterioscleroses can also be examined using, regarding the same blood vessel, a difference between a blood flow waveform of a blood vessel part and a waveform of RFV proportional to a blood flow volume of a surface layer blood vessel set forth above as shown in FIG. 16. Numeral 161 indicates a blood flow waveform and Numeral 162 indicates a waveform of RFV in FIG. 16. The phenomenon that the peak of RFV waveform appears later compared with the peak of blood flow waveform is a feature due to elasticity of the blood vessel. In the process in which a heart shrinks, first the blood flow of the blood vessel quickens, the blood flow volume increases, and blood is filled up to capacity by the normal diameter of the blood vessel. Since the heart shrinks further to push out blood, in the case of a flexible blood vessel with elasticity, it is expanded from the inside so that blood flow volume increases, while the blood flow rate decreases because the blood flow receives pressure in the counter direction with the vessel wall and the pressure acts as a brake. Therefore, the peak of RFV is considered to appear later compared with the peak of blood flow. The difference Δt between both peak positions is considered to vary depending on the degree of progress of arteriosclerosis. This Δt may be utilized for diagnosis as an index examining arteriosclerosis by quantifying it. Further, by obtaining electrocardiogram data at the same time as measuring a blood flow of an eye ground and then providing a time axis of a blood flow or RFV waveform of an eye ground referring to a waveform of the electrocardiogram, it is possible to analyze hemodynamics in each part more accurately.

In the present invention, as a method to separate a surface layer blood vessel from a background blood flow, it is possible to use a mask obtained by irradiating an eye ground with an incoherent light such as a light used generally for observing an eye ground, taking an image of an eye ground blood vessel and thresholding the image. The image of an eye ground blood vessel can be obtained by using an incoherent light such as a green LED capable of grasping easily outlines of a blood vessel, separating the light from a laser optical path using an optical filter and using an image sensor installed separately. A treatment for analyzing a blood flow by applying the mask to each map can be performed according to the method set forth above.

In the device of the present invention, since a blood flow increases rapidly at the contraction stage of the heart, a slight change of waveform may not be recognized due to insufficient time resolution of a series of blood flow maps calculated. In such a case, it is possible to improve time resolution in appearance by taking a spline interpolation into a blood flow waveform. When a small number of samples are provided for analysis, false results may come out by contrast since original data are insufficient in reliability. Therefore, it is possible to improve the accuracy of evaluating a blood flow waveform by adding a function that gives a warning when the number of samples does not reach a certain number.

The invention claimed is:

1. A blood flow image diagnosis device comprising:
a laser beam irradiation system that irradiates, with a laser beam, an observation region of a body tissue having a blood cell;
a light receiving system having a light receiver, including a plurality of pixels, that detects reflected light from the observation region of the body tissue;
an image capture section that continuously captures, based on a signal from the light receiver, a plurality of images for a specified time including one or more cardiac beats;
an image storage section that stores the plurality of images;
an arithmetic section that calculates a blood flow rate within the body tissue from a time variation of an output signal of each pixel corresponding to the plurality of the stored images; and
a display section that displays a two-dimensional distribution of the calculated blood flow rate as a blood flow map;
wherein
the arithmetic section separates, based on a plurality of blood flow maps covering the specified time including one or more cardiac beats, a blood flow of a surface layer blood vessel observed in a surface layer in the observation region of the body tissue from a background blood flow of a peripheral background region,
the display section distinguishably displays a first blood flow map of the surface layer blood vessel and a second blood flow map of the background blood flow,
the arithmetic section calculates and compares information on a blood flow including blood flow value, blood flow waveform, or blood vessel diameter in said first and second blood flow maps, and
the display section displays the calculated information,
wherein the arithmetic section:
calculates an amount of position-disparity, generated by movement of a measuring object, regarding said plurality of blood flow maps,
obtains an average blood flow map by compensating the plurality of the blood flow maps with the amount of position-disparity and superimposing the compensated plurality of the blood flow map,
obtains a mask image based on the average blood flow map by distinguishing a range with higher blood flow from a range with lower blood flow based on a threshold and excluding isolated points on the average blood flow map,
superimposes the mask image on each of the plurality of blood flow maps,
independently extracts the blood flow on the surface layer blood vessel and the background blood flow in a first region of the plurality of blood flow maps, respectively, and
obtains information on the blood flow of the surface layer blood vessel and the background blood flow.

2. The blood flow image diagnosis device according to claim 1,
wherein the arithmetic section:
obtains blood flow waveforms for the surface layer blood vessel and the background blood flow in one or more regions of the blood flow map, and quantifies a feature of one of the blood flow waveforms appearing upon either an increase or decrease of blood flow variation by heart beat or features of the blood flow waveforms, and the display section displays and compares the quantified feature with respect to the one or more regions of the blood flow map.

3. The blood flow image diagnosis device according to claim 1, wherein the arithmetic section obtains skewness of blood flow waveforms for the surface layer blood vessel and the background blood flow in one or more regions of the blood flow map, and the display section displays and compares the skewness of the blood flow waveforms with respect to the one or more regions of the blood flow map.

4. The blood flow image diagnosis device according to claim 1, wherein the arithmetic section:

determines blood flow waveforms for the surface layer blood vessel and the background blood flow in one or more regions of the blood flow map, integrates a blood flow value in a time in which one of the blood flow waveforms goes to a bottom from a peak, integrates a constant blood flow value, indicated as a difference between a peak value and a minimum value, in the same time, and quantifies a feature of one of the blood flow waveforms by obtaining a ratio of the integrated blood flow value and the integrated constant blood flow value, and the display section displays and compares the quantified feature with respect to the one or more regions of the blood flow map.

5. The blood flow image diagnosis device according to claim 1, wherein the arithmetic section:

obtains blood flow waveforms for the surface layer blood vessel and the background blood flow in one or more regions of the blood flow map, obtains respective amplitude values of the blood flow waveforms, and quantifies a feature of one of the blood flow waveforms by calculating a ratio of the corresponding amplitude value to an average blood flow value, and the display section displays and compares the quantified feature with respect to the one or more regions of the blood flow map.

6. The blood flow image diagnosis device according to claim 1, wherein the calculating and comparing information on a blood flow includes the blood flow value, and wherein the arithmetic section:

specifies one or more regions containing the surface layer blood vessel in the first blood flow map, separates, based on the specified one or more regions containing the surface layer blood vessel in the first blood flow map, the blood flow of the surface layer blood vessel from the background blood flow, extracts the blood flow value in the one or more regions, and independently calculates a respective average value for the surface layer blood vessel and the background blood flow, and the display section displays and compares the respective average value with respect to the one or more regions of the blood flow map.

7. The blood flow image diagnosis device according to claim 1, wherein the arithmetic section:

specifies one or more regions containing the surface layer blood vessel in the first blood flow map, separates, based on the specified one or more regions containing the surface layer blood vessel in the first blood flow map, the blood flow of the surface layer blood vessel from the background blood flow, calculates a total number of pixels in a region corresponding to the surface layer blood vessel, thereby calculates a numerical value proportional to a diameter of the surface layer blood vessel, and the display section displays and compares the numerical value.

8. The blood flow image diagnosis device according to claim 1, wherein the arithmetic section:

specifies one or more regions containing the surface layer blood vessel in the first blood flow map, separates, based on the specified one or more regions containing the surface layer blood vessel in the first blood flow map, the blood flow of the surface layer blood vessel from the background blood flow, specifies borderlines between the surface layer blood vessel and the background blood flow existing on both sides of the surface layer blood vessel, and calculates a diameter of the surface layer blood vessel on the basis of an interval of the borderlines, and the display section displays and compares the calculated diameter.

9. The blood flow image diagnosis device according to claim 1, wherein the blood flow image diagnosis device:

compares the calculated information with second information calculated by the arithmetic section on another blood flow image data with a different measurement date or time, calculates an increase-decrease rate of the calculated information based on the second information, and displays and compares the increase-decrease rate.

10. The blood flow image diagnosis device according to claim 1, wherein the blood flow image diagnosis device:

makes a mask, for separating the blood flow of the surface layer blood vessel from the background blood flow, by utilizing light and dark parts of a retina image which is obtained by irradiating an incoherent light to an eye ground, applies the mask to the plurality of the blood flow maps, and obtains information on blood flow at a surface layer site and a background site on each of the blood flow maps to which the mask is applied.

11. The blood flow image diagnosis device according to claim 1, wherein the arithmetic section:

specifies one or more rectangular regions containing the surface layer blood vessel in the blood flow map so as to have a longer direction along a course of the surface layer blood vessel, separates, based on the specified one or more rectangular regions, the blood flow of the surface layer blood vessel from the background blood flow, totals a value that is obtained by subtracting a background blood flow value from a blood flow value in each pixel in a region corresponding to the surface layer blood vessel, and obtains a value proportional to a blood flow volume of the surface layer blood vessel by dividing the totaled value by a longitudinal pixel count of the rectangular region, and the display section displays the obtained value, and compares the value in each of the specified one or more rectangular regions mutually or with a value measured at a different time.

12. The blood flow image diagnosis device according to claim 11, wherein the blood flow image diagnosis device:

analyzes an appearance that the value proportional to the blood flow volume obtained by the arithmetic section changes during measurement, displays analysis results as a waveform of blood flow volume, and analyzes and quantifies a feature of the waveform.

13. The blood flow image diagnosis device according to claim 1, wherein the arithmetic section:

distinguishes, in a region containing a number of retina vessels extending from an optic nerve head to all sides, an artery and a vein by analyzing a blood flow waveform in a blood vessel crossing a borderline of the region, and analyzes a blood flow volume and/or the blood flow waveform, respectively, and the display section displays analysis results near each blood vessel, saves the results as data files or compares the results with results measured on a different date.

14. The blood flow image diagnosis device according to claim 1, wherein the arithmetic section calculates, in a region containing a number of retina vessels extending from an optic nerve head to all sides, each total blood flow volume of an artery and a vein going in and out through a boundary of the region, and compares a value of a ratio of each total blood flow volume or compares the total blood flow volume with one measured on a different date.

15. The blood flow image diagnosis device according to claim 1, wherein the arithmetic section:

calculates, in a region containing a number of retina vessels extending from an optic nerve head to all sides, a ratio of blood flow volume to a blood vessel diameter with respect to blood vessels passing through the region, and the display section displays the calculated ratio using a figure or color.

16. The blood flow image diagnosis device according to claim 1, wherein the arithmetic section:

analyzes, in surface layer blood vessels crossing mutually or a piece of the surface layer blood vessel with branched vessels in the blood flow map, a blood flow volume or a blood flow waveform of each blood vessel, and the display section displays analysis results near each surface layer blood vessel, saves the results as data files or compares the results with results measured on a different date.

17. The blood flow image diagnosis device according to claim 1, wherein the calculating and comparing information on a blood flow includes the blood flow value, and wherein the arithmetic section:

analyzes, in the surface layer blood vessel in the blood flow map, each time variation of waveforms regarding a blood flow volume and the blood flow value of the surface layer blood vessel, calculates a difference of a peak position between the waveforms, and displays the calculated difference using a figure or color.

18. A blood flow image diagnosis method comprising:

irradiating, with a laser beam, an observation region of a body tissue having a blood cell;

detecting reflected light from the observation region of the body tissue;

capturing, on the basis of the detected reflected light, a plurality of images for a specified time including one or more cardiac beats, each of the plurality of images comprising pixels;

storing the plurality of images;

calculating a blood flow rate within the body tissue from a time variation of an output signal of each pixel corresponding to the plurality of the stored images; and displaying a two-dimensional distribution of the calculated blood flow rate as a blood flow map;

wherein the calculating comprises separating, on the basis of a plurality of blood flow maps covering the specified time including one or more cardiac beats, a blood flow of a surface layer blood vessel observed in a surface layer in the observation region of the body tissue from a background blood flow of a peripheral background region, the displaying comprises distinguishably displaying a first blood flow map of the surface layer blood vessel and a second blood flow map of the background blood flow, the calculating further comprises calculating and comparing information on a blood flow including blood flow value, blood flow waveform, or blood vessel diameter in said first and second blood flow maps, and the displaying further comprises displaying the calculated information, wherein the calculating the information on the blood flow comprises:

calculating an amount of position-disparity, generated by movement of a measuring object, regarding said plurality of blood flow maps, obtaining an average blood flow map by compensating the plurality of the blood flow maps with the amount of position-disparity and superimposing the compensated plurality of the blood flow maps, obtaining a mask image based on the average blood flow map by distinguishing a range with higher blood flow from a range with lower blood flow based on a threshold and excluding isolated points on the average blood flow map, superimposing the mask image on each of the plurality of blood flow maps, independently extracting the blood flow on the surface layer blood vessel and the background blood flow in a first region of the plurality of blood flow maps, respectively, and obtaining information on the blood flow of the surface layer blood vessel and the background blood flow.

* * * * *